United States Patent [19]

Coppess

[11] Patent Number: 4,580,555
[45] Date of Patent: Apr. 8, 1986

[54] PORTABLE PELVIC AND LEG SPLINT

[76] Inventor: Stacey Coppess, 704 S. Pacific, Oceanside, Calif. 92054

[21] Appl. No.: 590,851

[22] Filed: Mar. 19, 1984

[51] Int. Cl.⁴ ............................................. A61F 5/04
[52] U.S. Cl. ................................................ 128/89 R
[58] Field of Search ............... 128/83, 89 R, 87 R, 128/94; 5/82 B, 82 R

[56] References Cited

U.S. PATENT DOCUMENTS 1,916,789  4/1933  Fordham ........................... 128/83
4,151,842  5/1979  Miller ............................ 128/87 R
4,174,709  11/1979  Maddux ......................... 128/87 R
4,276,875  7/1981  Sandegard ..................... 128/89 R Primary Examiner—John D. Yasko
Attorney, Agent, or Firm—John J. Murphey

[57] ABSTRACT

A portable pelvic and leg transport splint comprising a long, narrow pad of two layers of nylon cloth containing a series of parallel stiff slats sewn in individual tubular pockets therebetween for positioning behind the patient's legs from pelvis to ankles and further containing a pair of flaps to wrap around the pelvis and a pair of flaps to wrap around the legs and straps to immobilize the patient on the pad and under the flaps and handles to pick up the patient immobilized in the pad for transportation.

2 Claims, 4 Drawing Figures

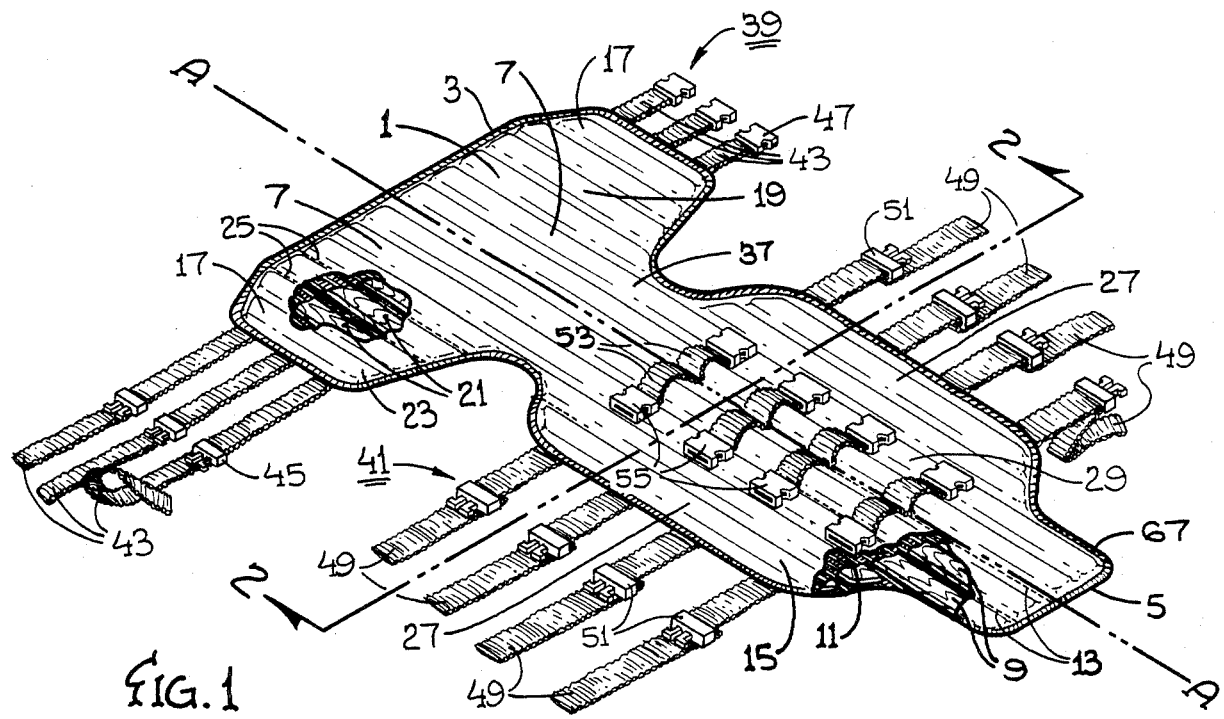
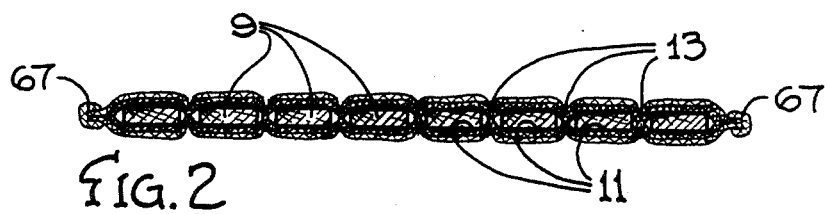
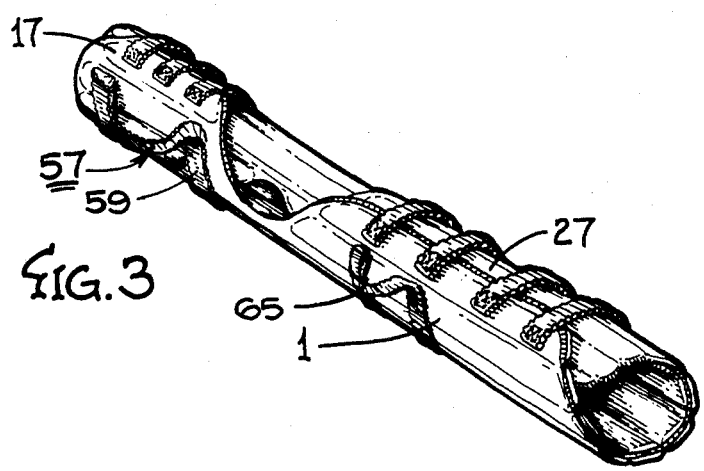

PORTABLE PELVIC AND LEG SPLINT

FIELD OF THE INVENTION

This invention pertains to the field of medical apparatus, especially body splints. More particularly, this invention concerns portable body splints for use in transporting persons injured in and about the pelvis and legs from accident scenes to hospitals, usually via ambulance.

BACKGROUND OF THE INVENTION

First aid immobilization techniques for broken arms and legs have advanced from the old wooden splint to inflated balloon and the like. Unfortunately, no such advancement has occasioned the far more dangerous injury to the pelvis and hips. Presently, the common first aid treatment is to lay the patient on a stretcher and load, transport and unload the injured patient still using the stretcher.

A stretcher is strictly a sling-type device, usually a canvas cloth supported by a stiff wood-frame perimeter. This construction causes the patient to sway and be jostled about during transportation. Such is a dangerous practice with pelvic and hip injuries; the close proximity of arteries and major veins to the pelvic girdle raises the possibility that any such body movement may cause the fractured bones to pinch, tear, or lacerate one of them. Since the stretcher is long, it often requires the injured patient to be dragged away from the accident scene before being placed thereon thus amplifying the pelvic and leg injuries. In addition, the stretcher is quite long and, although foldable when empty to allow entry through small doors and passageways, is often too long to properly carry the injured patient out through these same openings. Thus, there is yet to be developed a suitable device for direct application to the pelvic or leg-injured patient, at or near the accident scene, that allows the injury to be immobilized during transportation to the care facility.

BRIEF SUMMARY OF THE INVENTION

This invention is a portable pelvic and leg transport splint that overcomes these aforementioned problems. This portable splint comprises a narrow pad made of staves or slats for positioning under the injured patient from pelvis to ankles and has flaps that fold up around the legs, hips and pelvis to be strapped together and to the pad to immobilize these body parts. Soft handles are conveniently located under the pad to allow the splinted patient to be picked up and transported. This device allows the patient to sit up or lean forward thus allowing the device to be slipped under the patient at the scene of the accident to avoid aggravation of the injuries. In addition, the design of this inventive splint allows it to be rolled into a tight roll for ease in storage and carrying.

Accordingly, the main object of this invention is a portable splint for immobilizing the injured pelvic and/or leg area of a patient and for transporting this immobilized patient from the accident scene to the hospital. Other objects include a portable transport device that will render an injured patient completely immobile at the scene of the accident, during loading and transportation to a care facility and during unloading thereof; a splint that is easy and convenient to use in small spaces, that can be lifted to carry the patient without jostling the injury area, and that can be rolled up for convenient transportation and storage when not in use. These and other objects of the invention will become more apparent by reading the following Description of the Preferred Embodiment along with the Drawings appended hereto. The scope of protection sought by the inventor can be realized from a fair reading of the Claims that conclude this specification.

DESCRIPTION OF THE DRAWINGS

FIG. 1 is a perspective view of the portable pelvic and leg traction splint of this invention.

FIG. 2 is a sectional end view of the splint taken along lines 2—2 in FIG. 1.

FIG. 3 is a perspective view of the splint in its rolled up configuration.

DESCRIPTION OF THE PREFERRED EMBODIMENT

Figure 4:
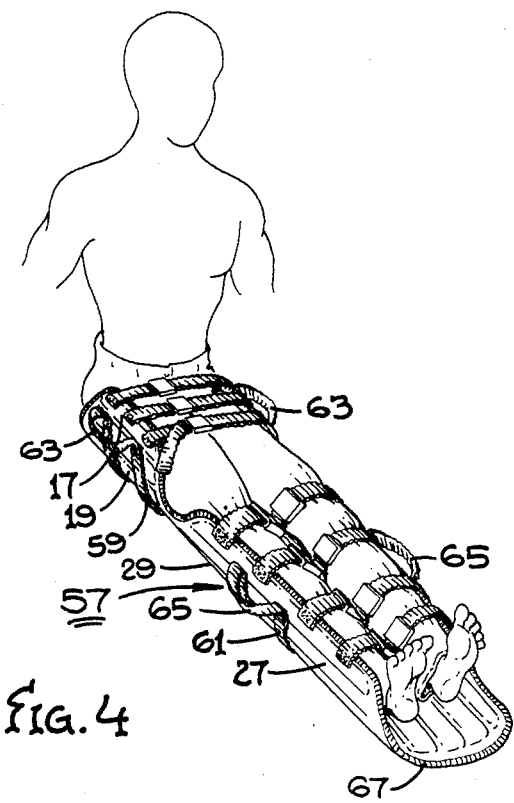
FIG. 4 is a perspective view of the splint showing its use with a patient immobilized therein.

FIG. 1 shows the splint of this invention to comprise an elongated narrow pad 1 terminating in opposed ends 3 and 5 respectively that are separated by elongated sides 7 and comprised of a series or plurality of narrow, elongated stiff slats or staves 9 in side-by-side arrangement, such as by each being individually housed in its own tubular pocket 11, sewn along lines 13 in a cover 15 for independent parallel movement therebetween. Said staves 9 may be made of wood or plastic as long as they are stiff and supportive of the patient's weight. Cover 15 should be strong and flexible while not stretchable; a convenient material is two (2) layers of woven 400 denier nylon Pack ® cloth. Pad 1 is to be placed or positioned behind the patient's legs from pelvis to ankles as shown in FIG. 4.

A first narrow pair of flaps 17 extend from sides 7 in the pelvic support area 19 of pad 1 near pad end 3 that comprise the same configuration of a plurality of stiff slats or staves 21 in side-by-side arrangement (see FIG. 2) such as by being each individually housed in its own tubular pocket 23 sewn along lines 25 in an extension of cover 15 for independent parallel movement therebetween. Said flaps 17 are adapted to be folded or wrapped up around the outside of the patient's pelvis as shown in FIG. 4.

A second pair of wider flaps 27 spaced apart from flaps 17 extends from the pad sides 7 in the leg support area 29 and comprise the same configuration of a plurality of stiff slats or staves 31 in side-by-side arrangement, such as by being each individually housed in its own tubular pocket 33, sewn along lines 35 in an extension of cover 15 for independent parallel movement therebetween. Said flaps are adapted to be folded or wrapped up around the outside of the patient's legs as shown in FIG. 4.

Between first and second flaps 17 and 27 is a narrow area 37 in pad 1 which acts as a transitional support area for the buttocks or thereabouts and needs no flaps but merely to interconnect pelvic support area 19 and leg support area 29.

A first strap means 39 and a second strap means 41 are provided to hold first pair of flaps 17 together and second pair of flaps 27 against pad 1 respectively to immobilize the patient's pelvis and legs on pad 1 as shown in FIG. 4. Means 39 and 41 may be of a wide variety of constructions such as leather belts, ropes or Velcro ® straps. It is preferred, however, to have them comprised of a plurality of strong, woven polypropylene webbing such as 400 Poly ® one or one and one-half inch wide belts. Means 39 is shown in FIG. 1 to comprise two sets of belts 43 attached to, such as by being sewn to, the ends of first flaps 17 and containing respectively adjustable male and female snap-connectors 45 and 47. Said snap-connectors allow quick connection and rapid belt length adjustment to quickly immobilize the patient's pelvis as fast as possible. A number of snap-connectors may be used; one preferred such snap-connector is a Fastex ® Fastener SR-1½ or Sr-1 made by Fastex Co., Des Plaines, Ill. 90016.

Second strap means 41 require the same properties and is shown to comprise a plurality of straps 49, such as 400 Poly ® belts as described earlier, attached along the outer edge of wide flaps 27 each containing an adjustable male snap-connector 51. A pair of short straps 53 are attached such as by sewing along the centerline of A—A of pad 1 midline their partner straps such as straps 49 and terminate in female snap-connectors 55 of the type hereinbefore described. While the ends of flaps 17 will be secured together about the pelvis, by first means 39, second means 41 operate to strap each leg independently to pad 1 using one flap 27 for each leg.

As can be more clearly shown in FIG. 4, a third strap means 57 is provided to enable the splint to be picked up by two individuals to transport a patient immobilized therein, such as from the accident scene to an ambulance or an ambulance to the emergency room of a care center. Said means comprise a closed loop of strap or webbing 59 under pelvic support area 19 sewn or otherwise attached to the underside of pad 1 and a double-loop strap or webbing 61 under leg support area 29, sewn or otherwise attached to pad 1 and having a pair of loose loops or handles 63 and 65 on each side of pad 1 for grasping to lift the patient.

For good looks and to prevent unravelling of the cloths that make up pad 1, said pad is surrounded about its outer edge with a binding tape 67 such as ¾ inch nylon binding tape. FIG. 3 shows how pad 1 and the flaps may be conveniently rolled up into a tight roll, owing to the independent movement allowed each slat, to form a tight, easily stored and easily carried roll.

What is claimed is:

1. A portable pelvic and leg transport splint comprising an elongated narrow pad for positioning behind the patient's legs from pelvis to ankles and containing a series of narrow, elongated stiff staves in side-by-side arrangement, each adapted for independent parallel movement therebetween, said pad comprised of:
   (a) a pelvic support area containing a first pair of flaps along the sides of said pad near one end thereof for wrapping up around the patient's pelvis;
   (b) a leg support area spaced apart from said pelvic support area containing a second pair of flaps along the sides of said pad for wrapping up around the outside of the patient's legs;
   (c) first and second strap means to fasten said first and second pairs of flaps around the patient's pelvis and legs respectively to immobilize the patient in said pad; and,
   (d) third strap means comprising:
      (i) a closed loop of strap under said pelvic support area attached to the underside of said pad terminating in free handles under said first pair of laps; and,
      (ii) a closed loop of strap under said leg support area attached to the underside of said pad terminating in free handles under said second pair of flaps for lifting said splint and transporting a patient immobilized therein.

2. A portable pelvic and leg transport splint comprising:
   (a) an elongated, narrow pad having opposed ends separated by elongated sides and containing a series of narrow, elongated parallel stiff slats, in side-by-side arrangement, each adapted for independent parallel movement therebetween, spanning said opposed ends, said pad adapted to be placed along the back of a patient's legs from pelvis to ankles:
   (b) a first pair of flaps extending from opposite sides of said pad in the area from the patient's pelvis for folding up around the outside of the patient's pelvis;
   (c) a second pair of flaps extending from opposite sides of said pad in the area of the patient's thighs to ankles for folding up around the outside of the patient's legs;
   (d) a first and second strap means to fasten said first and second pairs of flaps around the patient's pelvis and legs respectively to immobilize the patient in said pad; and,
   (e) a third means comprising:
      (i) a closed loop of webbing under said pelvic support area attached to the underside of said pad terminating in free handles under said second pair of flaps; and,
      (ii) a closed loop of webbing under said leg support area attached to the underside of said pad terminating in free handles under said second pair of flaps for lifting said splint and transporting a patient immobilized therein.

* * * * *